(12) United States Patent
Pirmoradi et al.

(10) Patent No.: US 11,739,361 B2
(45) Date of Patent: Aug. 29, 2023

(54) METHOD FOR IMMOBILIZING ENZYMES USING ULTRAVIOLET CURING

(71) Applicant: Palo Alto Research Center Incorporated, Palo Alto, CA (US)

(72) Inventors: Fatemeh Nazly Pirmoradi, Menlo Park, CA (US); Gregory Whiting, Menlo Park, CA (US)

(73) Assignee: XEROX CORPORATION, Norwalk, CT (US)

(*) Notice: Subject to any disclaimer, the term of this patent is extended or adjusted under 35 U.S.C. 154(b) by 580 days.

(21) Appl. No.: 16/731,323

(22) Filed: Dec. 31, 2019

(65) Prior Publication Data

US 2021/0198714 A1 Jul. 1, 2021

(51) Int. Cl.
*C12Q 1/00* (2006.01)
*C12N 13/00* (2006.01)
*C12N 11/08* (2020.01)

(52) U.S. Cl.
CPC .............. *C12Q 1/001* (2013.01); *C12N 11/08* (2013.01); *C12N 13/00* (2013.01)

(58) Field of Classification Search
CPC ............ C12Q 1/001; C12N 11/02–098; C12N 13/00; G01N 33/525; G01N 27/3271–3278
See application file for complete search history.

(56) References Cited

U.S. PATENT DOCUMENTS

2010/0255120 A1* 10/2010 Collier ................. C12N 11/087
424/661
2014/0322617 A1* 10/2014 Wang ................... H01M 4/8807
427/553

FOREIGN PATENT DOCUMENTS

EP 2225388 9/2010

OTHER PUBLICATIONS

Morgan, M.T. "Novel Surface Activation Technique Using Energy Curable Material for Theproduction of Bioactive Packaging" USDA NRI Grant Report, 2010, 5 pgs (Year: 2010).*
Kothapalli et al. "Comparison of Kinetic Profile of Free and Immobilized Glucose Oxidase, Immobilized on Low-Density Polyethylene Using UV Polymerization" Journal of Food Science—vol. 72, Nr. 9, 2007, pp. C487-C482 (Year: 2007).*
Rohm et al. "UV-Polymerizable Screen-Printed Enzyme Pastes" Anal, Chem. 1995, 67, 2304-2307 (Year: 1995).*
Kim et al., "Non-invasive mouthguard biosensor for continuous salivary monitoring of metabolites", Analyst, 2014. 139 (7): p. 1632-1636.
Jia et al., "Electrochemical Tattoo Biosensors for Real-Time Non-invasive Lactate Monitoring in Human Perspiration", Analytical Chemistry, 2013. 85(14): p. 6553-6560.
Mersal et al., "Optimisation of the composition of a screen-printed acrylate polymer enzyme layer with respect to an improved selectivity and stability of enzyme electrodes", Biosensors and Bioelectronics, 2004. 20(2): p. 305-314.
Nagata et al., "A glucose sensor fabricated by the screen printing technique" Biosensors and Bioelectronics, 1995. 10 (3): p. 261-267.

* cited by examiner

*Primary Examiner* — Thane Underdahl
(74) *Attorney, Agent, or Firm* — Mueting Raasch Group

(57) ABSTRACT

A method comprises printing a conductive ink on a substrate to form one or more electrodes and printing an electrode ink on one or more of the electrodes. The conductive and electrode inks are cured. Next, an enzyme ink layer is printed on at least one electrode, and the enzyme ink layer is cured with ultraviolet light. Each of the printing and curing processes are performed in an in-line process.

11 Claims, 5 Drawing Sheets

METHOD FOR IMMOBILIZING ENZYMES USING ULTRAVIOLET CURING

STATEMENT REGARDING FEDERALLY SPONSORED RESEARCH AND DEVELOPMENT

This invention is partially funded by Nano Bio Manufacturing Consortium (NBMC) under contract number FA8650-13-2-7311. The Government has certain rights to this invention.

TECHNICAL FIELD

This disclosure relates generally to methods for immobilizing enzymes using ultraviolet curing and methods of making enzyme inks for such immobilization.

BACKGROUND

Biosensors are analytical devices that convert a biological response into a quantifiable, and processable, signal. For example, an electrochemical biosensor uses a reaction between a target analyte and enzymes immobilized on an electrode of the sensor and a transducer material to measure current or voltage produced by the reactions. The current, or voltage, signal is transmitted to a controller for processing and/or display.

Fabricating biosensor transducer layers requires immobilizing enzymes without damaging the enzymes so that they can interact with the target analyte once the biosensor fabrication is complete. Traditional fabrication processes for enzymatic biosensors immobilize enzymes using secondary steps and/or additives that cannot be readily adopted for layer-by-layer processing. For example, certain processes involve forming multiple layers to prevent leaching. In other examples involving single layer designs, wet fabrication processes, such as electropolymerization, are used. While electropolymerization has been used as a standard process for enzyme immobilization, it involves forming the conducting polymer on a conducting substrate from polymerization solution.

Other enzyme immobilization techniques have even further increased complexity. Certain processes involve functionalization of the surface of the printed electrode. For example, with lactate oxidase immobilization, the surface of the electrode is functionalized with TTF (tetrathiafulvalene) and multiwall carbon nanotubes followed by tethering of LOx enzyme and a chitosan overlayer, all of which involves multiple air-drying steps during fabrication. Alternatively, an air-dried screen-printable enzyme layer may be produced by mixture of soluble (e.g., PVP-polyvinylpyrrolidone) and insoluble (e.g., PVB-polyvinylbutyral) polymers, but the air-drying step lengthens the total fabrication time. In another example, screen-printable UV-curable enzyme paste based on polymethacrylate is used for enzyme immobilization; however, because of the dense and non-porous structure of the acrylate polymer layer, additional steps and additives are required for efficient performance. The manufacturing cost, and complexity, for electrochemical biosensor fabrication could be reduced by using a single layer deposition technique for immobilized enzymes that could be incorporated into an in-line printing process.

SUMMARY

Embodiments described herein are directed to a method. The method includes printing a conductive ink on a substrate to form one or more electrodes and printing an electrode ink on one or more of the electrodes. The conductive and electrode inks are cured. Next, an enzyme ink layer is printed on at least one electrode, and the enzyme ink layer is cured with ultraviolet light. Each of the printing and curing processes are performed in an in-line process.

Other embodiments are directed to a formulation for an enzyme-containing ink. The formulation is configured to immobilize enzymes in a continuous printing process.

Further embodiments are directed to a method. The method includes providing a flexible substrate comprising one or more electrodes and printing an enzyme-containing ink on one or more of the electrodes. The enzymes are immobilized by ultraviolet curing, and the printing and immobilizing processes are performed in an in-line fabrication process.

The above summary is not intended to describe each disclosed embodiment or every implementation of the present disclosure. The figures and the detailed description below more particularly exemplify illustrative embodiments.

BRIEF DESCRIPTION OF THE DRAWINGS

The discussion below refers to the following figures, wherein the same reference number may be used to identify the similar/same component in multiple figures. However, the use of a number to refer to a component in a given figure is not intended to limit the component in another figure labeled with the same number. The figures are not necessarily to scale.

DETAILED DESCRIPTION

As discussed above, known fabrication processes of enzymatic biosensors are incompatible with in-line printing because the enzymes are immobilized using secondary steps that cannot be readily adapted to layer-by-layer processing, which involves depositing alternating layers of thin films/materials of oppositely charged materials. In contrast, embodiments described herein address a single layer enzyme immobilization method using solution-based printing techniques that may be used, for example, in the fabrication of electrochemical biosensors. In particular, the embodiments described herein enable realization of fully printed electrochemical biosensors. Unlike the processes discussed above, electrochemical biosensors are fabricated using a multi-material printing approach described herein where the one, or more, enzyme is immobilized in a single layer on the working electrode of a biosensor via printing and polymerization of a viscosity-modified enzyme ink.

The enzyme ink incorporates the enzyme molecules in a cross-linkable polymer matrix (e.g., hydrogel-based), which allows direct transport/exposure of analyte to the enzyme (i.e., enzymatic reaction) without a need for multiple additives in the ink or additional steps to facilitate this transport. In-line ultraviolet (UV) curing of the developed enzyme ink polymerizes the ink and entraps enzymes in a single layer. Thus, the need for secondary non-printing steps for enzyme immobilization is avoided. Using UV curing, rather than thermal curing, prevents the enzymes from being damaged (i.e., catalytic activity is maintained). UV curing can also be carried out rapidly, allowing further layers to be printed without delay when a layer-by-layer, or multi-layer, printing process is used.

Figure 1:
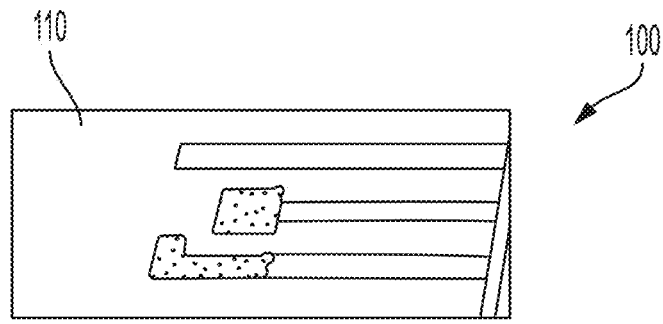
FIG. 1 is a top-down view of an electrochemical biosensor fabricated in accordance with certain embodiments.

Turning to FIG. 1, an electrochemical biosensor 100 fabricated in accordance with embodiments described herein is shown. As discussed further below, the electrochemical biosensor 100 may be printed on a flexible substrate 110 such that it may be usable in a variety of applications. For example, such electrochemical biosensors may be utilized in biomedical devices, including wearable diagnostics such as mouthguards. For example, mouthguards may incorporate glucose biosensors that utilize saliva to analyze glucose levels for people with diabetes. More broadly, the enzyme immobilization method may be applicable to other printing applications used in biomedical devices, other types of biosensors, diagnostics, wearable applications, printed electronics, flexible electronics, large area electronics, and with internet-of-things applications and systems, to name just a few. However, for explanatory, and non-limiting, purposes, the methods described herein are discussed in connection with fabricating an electrochemical biosensor.

Figure 2:
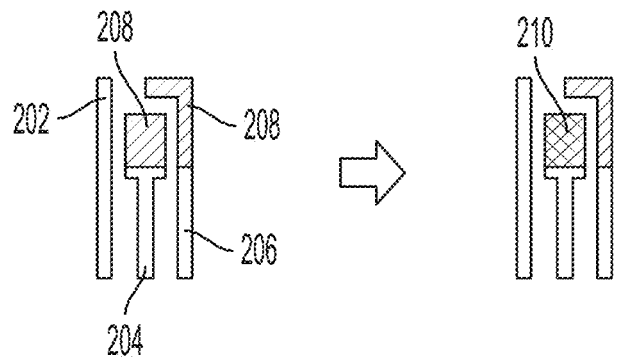
FIG. 2 is a schematic diagram of materials deposited to form an electrochemical biosensor in accordance with certain embodiments.

The materials deposited to form an electrochemical biosensor, in accordance with embodiments described herein, are illustrated in FIG. 2. The biosensor includes a reference electrode 202, working electrode 208 over/connected to 204, and counter electrode 208 over/connected to 206. The electrodes are formed by depositing conductive materials on a substrate 202, 204, 206 and creating contacts. Then, electrode ink 208 is deposited to form the working and counter electrodes over/connected to conductive material 204, 206. Next, an enzyme ink 210 is deposited on the working electrode 208 over/connected to 204 to provide an immobilized enzyme(s) in, for example, a hydrogel or other cross-linkable polymer. The deposition of each material may be performed via a variety of printing processes, for example, using an in-line printing process as described further below.

Figure 3:
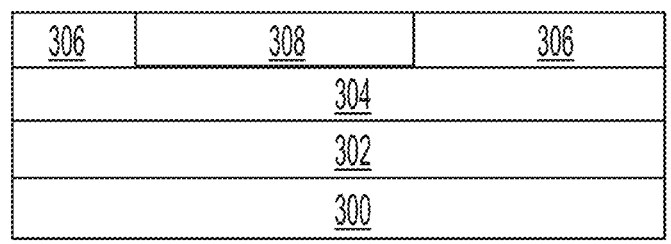
FIG. 3 is a cross-section of an electrochemical biosensor formed in accordance with certain embodiments.

FIG. 3 is a cross-section of an example electrochemical biosensor, such as is formed by the material deposition described above in connection with FIG. 2. The biosensor is formed on a substrate 300, which may be any rigid or flexible substrate that is suitable for printing thereon. Example substrate materials may include polyethylene naphthalate, polyethylene terephthalate, polymers, plastics, woven materials, glass, human or animal tissue, nails, paper/cardboard, and inside or over 3D printed materials. The biosensor layers may adhere to the substrate or may be removable once the layers have cured (e.g., peeled off). A conductive layer 302 forming electrodes and contacts is deposited on the substrate 300. The conductive layer 302 may comprise any variety of conductive materials including silver, silver/silver chloride, carbon, gold, platinum, and various combinations thereof. An electrode layer 304 providing an electrode ink, such as prussian blue-graphite, is deposited on the working and counter electrodes. An enzyme ink layer 308 is deposited over the working electrode, and an insulating layer 306 is deposited, by printing or other methods, over the surface to overlay the sensor parts requiring isolation. The enzyme ink 308 includes a photo curable polymer, a photo initiator, and one or more types of enzymes, as discussed further below.

Figure 4:
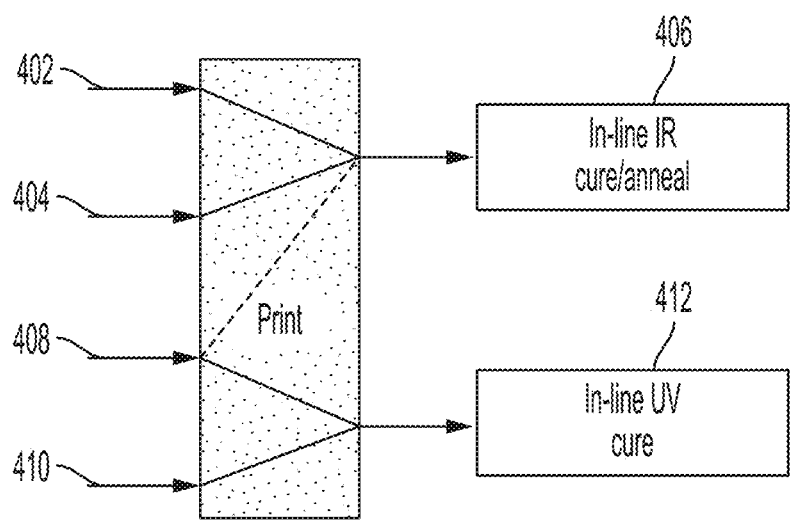
FIG. 4 is a diagram of a method for immobilizing enzymes in accordance with certain embodiments.

FIG. 4 illustrates an in-line printing fabrication process for an electrochemical biosensor. The process provides a single layer enzyme immobilization method using solution-based printing techniques. A conductive ink (e.g., Ag/AgCl) 402 and an electrode ink (e.g., prussian blue-graphite) 404 are extruded on a substrate (e.g., polyethylene naphthalate for flexible sensors) to form the sensor electrodes and any appropriate electrical connections. The conductive ink may be extruded first 402, or the conductive and electrode inks may be extruded together using layered printing techniques. The conductive and electrode inks are cured and/or annealed 406 as part of the fabrication process using, for example, infrared (IR) light. Each layer may be cured after deposition, or they may be cured together after both have been deposited. Printing dielectric is overlaid 408 on the sensor parts requiring insulation (e.g., connections), and the enzyme ink is printed 410 on the working electrode. The enzyme ink is subsequently cured using UV light 412 as part of the printing process to immobilize the enzymes over the working electrode.

Figure 5:
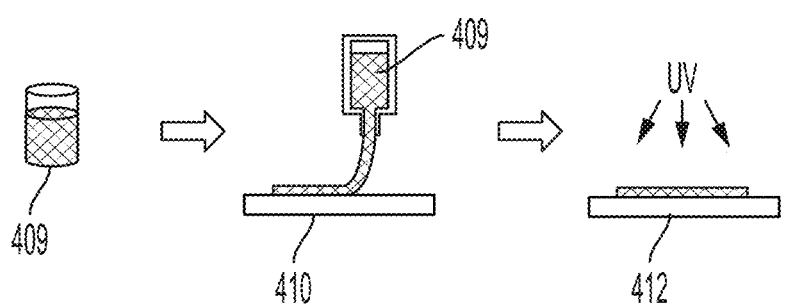
FIG. 5 is a diagram of a portion of a method for immobilizing enzymes in accordance with certain embodiments.

Fabricating the electrochemical biosensor using printing techniques is accomplished via the deposition and curing of the enzyme ink in an in-line process, which is described further in FIG. 5. In-line processing herein refers to fabrication processes that are performed subsequently and in close proximity to each other, for example, within one or more pieces of equipment such as one or more printing stations. In certain embodiments, the workpieces, e.g., electrochemical biosensors, are transported among processing steps without manual intervention (i.e., along a conveyor belt, or carried by cartridges). Subsequent printing and/or curing steps are each performed in about 2-60 seconds such that the in-line printing provides a rapid fabrication process. A printable, enzyme ink 409 is developed that forms a layer on the sensor working electrode via printing and in-line curing. Enzyme ink can be printed using a variety of printing techniques, including but not limited to, extrusion, inkjet, continuous inkjet, screen print, flexo, etc., for which the enzyme ink viscosity is modified. For example, a viscous enzyme ink 409 is extruded on the working electrode 410 and subsequently cured 412 using a UV light source. These steps 409-412 may be repeated as needed when a multi-layer deposition process is used for the enzyme layer of the working electrode. Once the enzymes are immobilized by the UV curing, the biosensor may be further processed including the deposition of further material layers.

Figure 6:
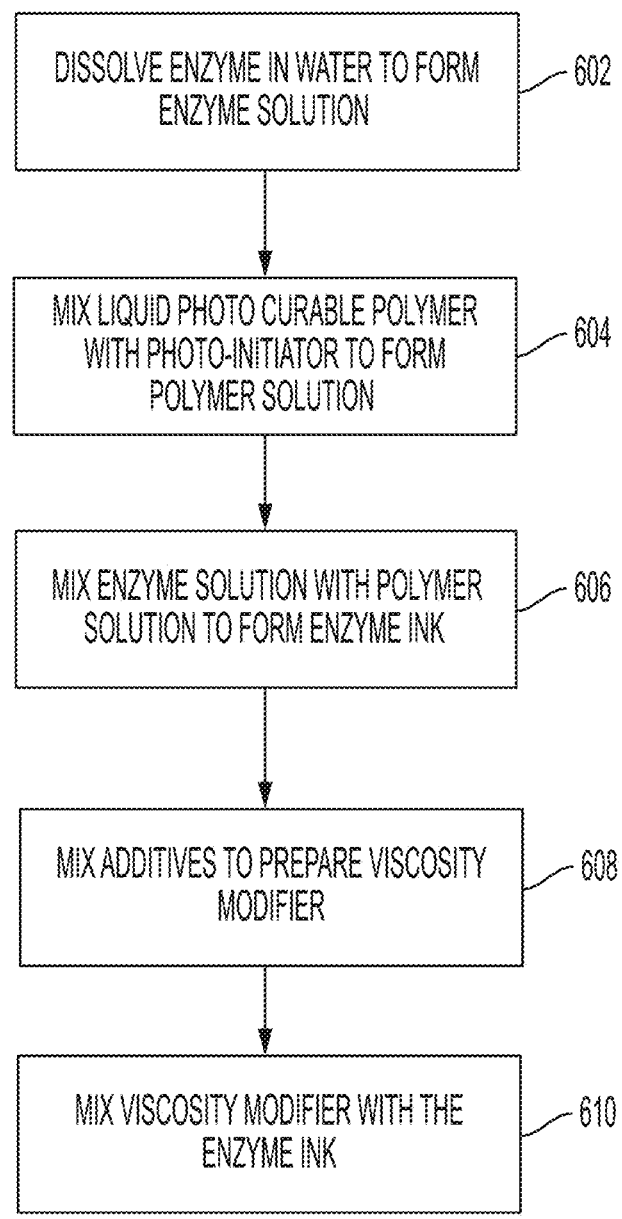
FIG. 6 is a flow chart of a method for making enzyme inks for enzyme immobilization in accordance with certain embodiments.

Formation of the enzyme ink is described in the flow chart of FIG. 6. The enzyme ink incorporates the enzyme molecules in a cross-linkable polymer matrix (e.g., a hydrogel) with a corresponding photo-initiator in the ink paste that allows curing with UV light and prevents damage to the enzyme layer by the analyte. The enzyme ink is prepared by dissolving one or more types of enzymes in water to form an enzyme solution 602. When more than one type of enzyme, or bioactive molecule, is incorporated into the enzyme ink layer, a variety of analytes may be detected by the sensor. In certain embodiments, the enzyme solution is prepared for a target concentration of 400 unit/ml in the final enzyme ink or paste. Separately, a liquid photo curable polymer is mixed with a photo-initiator to form a polymer solution 604. In certain embodiments, polyethylene glycol diacrylate (PEGDA) is used as the photo curable polymer and 2-hydroxy-2-methylpropiophenone (Darocur 1173) is used as the photo-initiator where liquid PEGDA monomer is mixed with 5% w/w photo-initiator to form the polymer solution. An enzyme ink is formed by mixing, or loading, the enzyme solution into the polymer solution 606.

At this point, the enzyme ink viscosity may be tuned for printing purposes by optionally adding a viscosity modifying agent, such as a biocompatible agent. The enzyme ink viscosity may be anywhere from 1-100,000 cp, for certain printing processes/environments. The enzyme ink is extruded at viscosities greater than 1,000 cp. One or more additives that will not affect the catalytic activity of the enzymes/sensor (i.e., biocompatible additives) may be mixed to prepare a viscosity modifier 608. An example additive is carboxymethyl cellulose, and in certain embodiments, it may be prepared using 3% w/w in 0.1M potassium phosphate buffer. The viscosity modifier is then mixed into the enzyme ink 610 to tune the viscosity for printing. Depending on the printing conditions (e.g., sensor materials and projected sensor use environment), the viscosity modifier may be mixed into the enzyme ink with a target of up to 50% viscosity modifier in the final enzyme ink. The enzyme ink may now be UV cured, for example, at 365 nm using a UV light source as part of the in-line fabrication process. The enzyme ink is developed so that the UV exposure required to cross-link the matrix polymer does not reduce the catalytic activity of the enzyme thereby maintaining the sensitivity of the biosensor (e.g., curing with about 2-60 seconds of UV exposure). Upon UV cross-linking of the printed enzyme polymer ink, the entrapped enzyme is immobilized within the polymer matrix layer over the working electrode.

In certain embodiments, the enzyme ink may incorporate further components such as leachable particles or leachable secondary polymers to form a more porous enzyme layer. If the photo curable polymer creates a dense enzyme ink that decreases the sensitivity of the working electrode, leachable components may be added to increase the porosity of the enzyme layer and improve the catalytic activity of the entrapped enzymes. When leachable components are included in the enzyme ink, one or more processing steps may be necessary to leach those materials from the polymer layer (e.g., an immersion step). Leachable materials may also be used as protective layers for the enzyme ink during fabrication of the biosensor and removed prior to completion of fabrication or use.

In further embodiments, the printed enzyme layer may be sandwiched between the electrode (e.g., working electrode) and another layer such as a porous overlay material/polymer. In even further embodiments, the enzyme ink and electrodes can be fabricated within and/or over a 3D printed object. Alternatively, the printed enzyme ink may be used to functionalize other structures such as resistive sensors and transistor structures, including thin-film transistors and organic electrochemical transistors.

EXAMPLES

Electrochemical biosensors were fabricated using the above-described methods and subsequently tested. For example, the effect of UV exposure on the enzyme activity was assessed by measuring glucose oxidase activity using microcalorimetry, where the curing was carried out using a 365 nm UV lamp with various exposure times. The results are summarized in Table 1 below.

TABLE 1

| Sample | UV Exposure(s) | $K_{cat}$ ($s^{-1}$) | $K_M$ (mM) |
|---|---|---|---|
| A (no UV exposure) | 0 | 331 | 17.6 |
| B | 13 | 299 | 13.6 |
| C | 42 | 320 | 10.3 |
| D | 64 | 336 | 16.6 |

Figure 7:
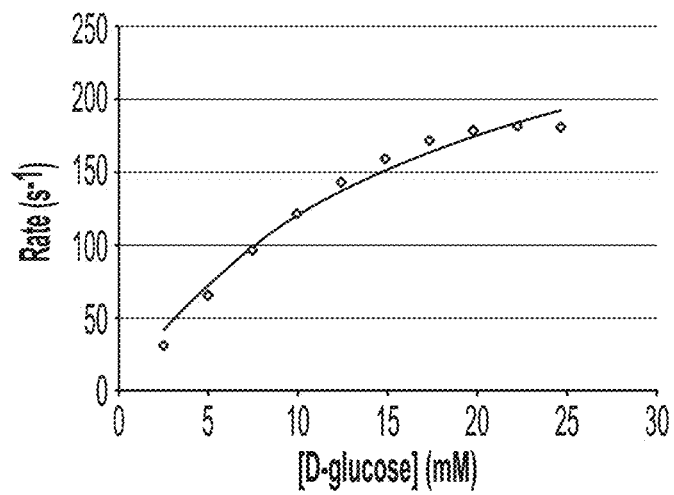
FIG. 7 is a graph showing rates of glucose oxidase without exposure to ultraviolet light.
Figure 8:
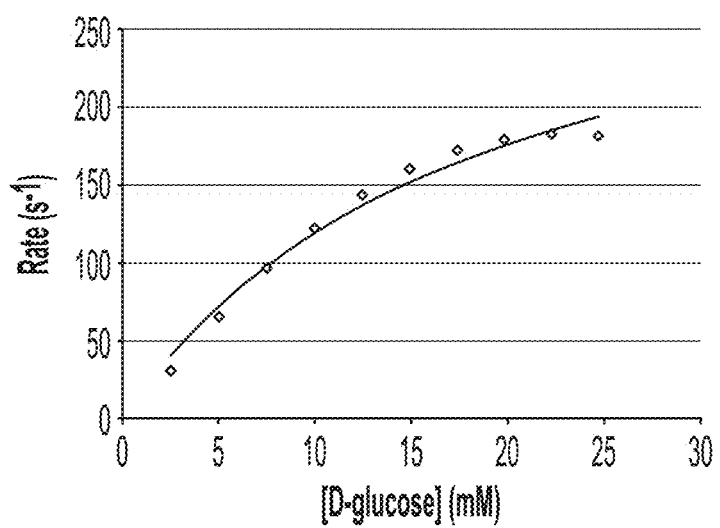
FIG. 8 is a graph showing rates of glucose oxidase after sixty-four seconds of exposure to ultraviolet light.

As can be seen, samples A-D were exposed to increasing amounts (time) of UV exposure. The third column indicates the rate of glucose oxidase conversion of glucose, and the fourth column indicates the concentration of glucose that permits the enzyme to achieve half of its maximum reaction rate. FIG. 7 is a graph of the glucose oxidase activity when the enzyme was not exposed to any UV light (i.e., Sample A), and FIG. 8 is a graph of the glucose oxidase activity when the enzyme was exposed to sixty-four seconds of UV light (i.e., Sample D). Comparison of the graphs of FIGS. 7 and 8 indicate that UV exposure does not have a significant impact on enzyme activity. Thus, the UV curing effectively immobilizes the enzyme without inhibiting catalytic activity.

Figure 9:
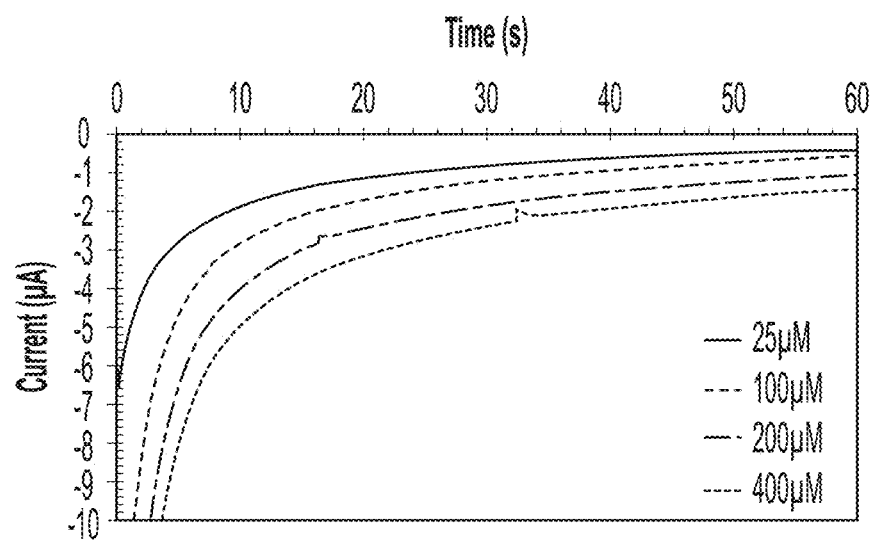
FIG. 9 is a graph of glucose measurement by an electrochemical biosensor fabricated in accordance with certain embodiments.
Figure 10:
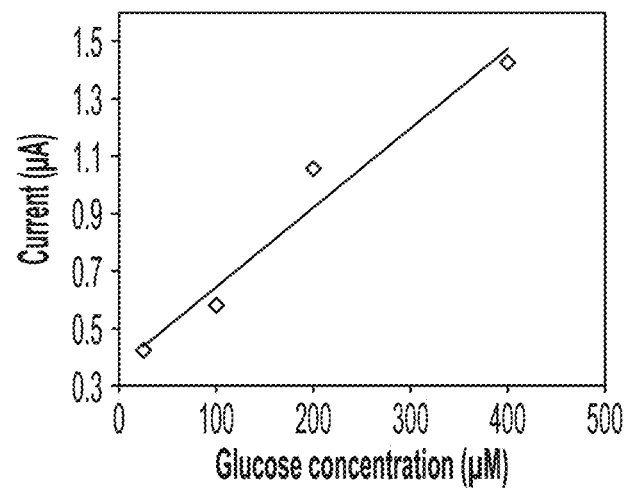
FIG. 10 is a graph of the measured current at sixty seconds for each glucose concentration of FIG. 9.

In addition, the effectiveness of an electrochemical glucose sensor fabricated according to the methods described herein was tested for a variety of glucose concentrations. Chronoamperometry measurement of the glucose sensor showed detection of glucose in a potassium phosphate buffer solution. The measurement was done in a 0.1 M potassium phosphate buffer solution containing 20 mM NaCl at pH 7. As shown in FIG. 9, the sensor detected a stabilized reaction, indicated by the respective plateaus in the results, for each of the tested concentrations of glucose (25 µM, 100 µM, 200 µM, 400 µM). FIG. 10 further indicates the strength of the detected signal (amount of current detected) for each glucose concentration after sixty seconds of sensing. As may be seen, FIG. 10 indicates linear behavior for the sensor as the glucose concentrations double.

As described herein, a viscous enzyme ink is developed that can be extruded using layer-by-layer printing techniques and UV cured using in-line processing to immobilize enzymes without inhibiting their catalytic activity. These fabrication techniques are useful in a variety of fields, including fabrication of electrochemical biosensors where heightened sensor flexibility and sensitivity are advantageous. The fabrication methods described herein further reduce manufacturing costs, timing, and complexity.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

The foregoing description has been presented for the purposes of illustration and description. It is not intended to be exhaustive or to limit the embodiments to the precise form disclosed. Many modifications and variations are possible in light of the above teachings. Any or all features of the disclosed embodiments can be applied individually or in any combination and are not meant to be limiting, but purely illustrative. It is intended that the scope of the invention be limited not with this detailed description, but rather, determined by the claims appended hereto.

What is claimed is:

1. A method, comprising:
    printing a conductive ink on or in a substrate to form one or more electrodes;
    printing an electrode ink on one or more of the electrodes;
    curing the conductive and electrode inks to form the one or more electrodes with a conductive ink layer under or connected to an electrode ink layer;
    printing an enzyme ink layer on the electrode ink layer of at least one electrode; and
    curing the enzyme ink layer with ultraviolet light, wherein each of the printing and curing processes are performed in an in-line process.

2. The method of claim 1, wherein the enzyme ink layer is a multi-layer structure and printing the enzyme ink layer comprises printing a first enzyme ink layer, curing the first enzyme ink layer with ultraviolet light, and printing a second enzyme ink layer on the first enzyme ink layer.

3. The method of claim 1, further comprising printing one or more material layers on the cured enzyme ink layer.

4. The method of claim 1, wherein the substrate is flexible.

5. The method of claim 1, wherein the substrate is a 3D object.

6. The method of claim 1, wherein curing the enzyme ink layer comprises exposing the enzyme ink to ultraviolet light for about 2 to 60 seconds.

7. The method of claim 1, wherein printing the enzyme ink layer comprises extruding the enzyme ink on at least one electrode in about 2 to 60 seconds.

8. The method of claim 1, further comprising leaching materials from the cured enzyme ink.

9. The method of claim 1, wherein the cured enzyme ink layer is a transducer layer.

10. The method of claim 9, wherein the cured enzyme ink layer is a biosensor transducer layer.

11. The method of claim 1, further comprising printing dielectric material on one or more portions of the electrode ink layer.

* * * * *